US012642579B2

(12) United States Patent
Allen, IV

(10) Patent No.: US 12,642,579 B2
(45) Date of Patent: Jun. 2, 2026

(54) ELECTROSURGICAL FORCEPS WITH TISSUE RESONANCE DETECTION

(71) Applicant: Covidien LP, Mansfield, MA (US)

(72) Inventor: James D. Allen, IV, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 859 days.

(21) Appl. No.: 17/752,971

(22) Filed: May 25, 2022

(65) Prior Publication Data

US 2022/0378496 A1 Dec. 1, 2022

Related U.S. Application Data

(60) Provisional application No. 63/193,654, filed on May 27, 2021.

(51) Int. Cl.
*A61B 18/14* (2006.01)
*A61B 18/00* (2006.01)

(52) U.S. Cl.
CPC .. *A61B 18/1445* (2013.01); *A61B 2018/0063* (2013.01); *A61B 2018/00642* (2013.01); *A61B 2018/00702* (2013.01); *A61B 2018/0072* (2013.01); *A61B 2018/00761* (2013.01); *A61B 2018/00767* (2013.01); *A61B 2018/00857* (2013.01)

(58) Field of Classification Search
CPC ................. A61B 18/1445; A61B 2018/00857
See application file for complete search history.

(56) References Cited

U.S. PATENT DOCUMENTS

| 5,752,973 A | 5/1998 | Kieturakis |
| 5,792,135 A | 8/1998 | Madhani et al. |
| 5,848,986 A | 12/1998 | Lundquist et al. |
| 6,817,974 B2 | 11/2004 | Cooper et al. |
| 7,799,028 B2 | 9/2010 | Schechter et al. |

(Continued)

FOREIGN PATENT DOCUMENTS

| EP | 2783653 A1 | 10/2014 |
| WO | 2017136710 A2 | 8/2017 |

OTHER PUBLICATIONS

Extended European Search Report issued in corresponding European Application No. 20154024.2 dated Jun. 26, 2020, 9 pages.

(Continued)

*Primary Examiner* — Linda C Dvorak
*Assistant Examiner* — Ryan T Clark

(57) ABSTRACT

A surgical instrument includes a housing having an elongated shaft extending distally therefrom and configured to support an end effector assembly at a distal end thereof. The end effector assembly includes first and second jaw members each having a tissue sealing plate disposed thereon and adapted to connect to an electrosurgical energy source for delivery thereto upon activation thereof. A sensor is disposed on one (or both) of the tissue sealing plates and is configured to communicate data relating to tissue disposed between the first and second jaw members to the electrosurgical energy source for correlation to a resonance frequency of the tissue. The resonance frequency of the tissue, in turn, is used to adjust one or more parameters associated with the delivery of electrosurgical energy to the tissue upon activation thereof.

15 Claims, 5 Drawing Sheets

(56) References Cited

U.S. PATENT DOCUMENTS

| | | | |
|---|---|---|---|
| 7,861,906 | B2 | 1/2011 | Doll et al. |
| 7,918,230 | B2 | 4/2011 | Whitman et al. |
| 8,579,176 | B2 | 11/2013 | Smith et al. |
| 9,055,961 | B2 | 6/2015 | Manzo et al. |
| 9,474,569 | B2 | 10/2016 | Manzo et al. |
| 2002/0099371 | A1 | 7/2002 | Schulze et al. |
| 2002/0177842 | A1 | 11/2002 | Weiss |
| 2003/0125734 | A1 | 7/2003 | Mollenauer |
| 2003/0208186 | A1 | 11/2003 | Moreyra |
| 2006/0022015 | A1 | 2/2006 | Shelton et al. |
| 2006/0025811 | A1 | 2/2006 | Shelton |
| 2006/0161138 | A1 | 7/2006 | Orban et al. |
| 2007/0233052 | A1 | 10/2007 | Brock |
| 2007/0282358 | A1 | 12/2007 | Remiszewski et al. |
| 2008/0015631 | A1 | 1/2008 | Lee et al. |
| 2010/0274265 | A1 | 10/2010 | Wingardner et al. |
| 2010/0292691 | A1 | 11/2010 | Brogna |
| 2011/0118707 | A1 | 5/2011 | Burbank |
| 2011/0118708 | A1 | 5/2011 | Burbank et al. |
| 2011/0118709 | A1 | 5/2011 | Burbank |
| 2011/0118754 | A1 | 5/2011 | Dachs, II et al. |
| 2014/0276723 | A1 | 9/2014 | Parihar et al. |
| 2016/0058492 | A1* | 3/2016 | Yates ................. A61B 18/1233 |
| | | | 606/34 |
| 2016/0066982 | A1 | 3/2016 | Marczyk et al. |
| 2017/0042560 | A1 | 2/2017 | Lee et al. |
| 2019/0201042 | A1* | 7/2019 | Nott ...................... A61B 34/76 |

OTHER PUBLICATIONS

Wu et al., "Design of a Modular Continuum-Articulated Laparoscopic Robotic Tool with Decoupled Kinematics", IEEE Robotics and Automation Letters, vol. 4, No. 4, Oct. 2019, pp. 3545-3552.
Extended European Search Report issued in corresponding European Application No. 20157439.9 dated Jun. 25, 2020, 9 pages.

* cited by examiner

ELECTROSURGICAL FORCEPS WITH TISSUE RESONANCE DETECTION

CROSS REFERENCE TO RELATED APPLICATION

This application claims the benefit of U.S. Provisional Application Ser. No. 63/193,654 filed May 27, 2021, the entire contents of which being incorporated by reference herein.

BACKGROUND

1. Technical Field

The present disclosure relates generally to the field of surgical instruments. In particular, the disclosure relates to electrosurgical forceps that is configured to identify the resonance frequency of tissue prior to or during activation.

2. Background of Related Art

Instruments such as electrosurgical forceps are commonly used in open and endoscopic surgical procedures to coagulate, cauterize and seal tissue. Such forceps typically include a pair of jaw members that can be controlled by a surgeon to grasp targeted tissue, such as, e.g., a blood vessel. The jaw members may be approximated to apply a mechanical clamping force to the tissue, and are associated with at least one electrode to permit the delivery of electrosurgical energy to the tissue. The combination of the mechanical clamping force and the electrosurgical energy has been demonstrated to join adjacent layers of tissue captured between the jaw members. When the adjacent layers of tissue include the walls of a blood vessel, sealing the tissue may result in hemostasis, which may facilitate the transection of the sealed tissue. A detailed discussion of the use of an electrosurgical forceps may be found in U.S. Pat. No. 7,255,697 to Dycus et al.

A bipolar electrosurgical forceps typically includes opposed electrodes disposed on clamping faces of the jaw members. The electrodes are charged to opposite electrical potentials such that an electrosurgical current may be selectively transferred through tissue grasped between the electrodes. To effect a proper seal, particularly in relatively large vessels, two predominant mechanical parameters must be accurately controlled; the pressure applied to the vessel, and the gap distance established between the electrodes.

Both the pressure and gap distance influence the effectiveness of the resultant tissue seal. If an adequate gap distance is not maintained, there is a possibility that the opposed electrodes will contact one another, which may cause a short circuit and prevent energy from being transferred through the tissue. Also, if too low a force is applied the tissue may have a tendency to move before an adequate seal can be generated. The thickness of a typical effective tissue seal is optimally between about 0.001 and about 0.006 inches. Below this range, the seal may shred or tear and above this range the vessel walls may not be effectively joined. Closure pressures for sealing large tissue structures preferably fall within the range of about 3 kg/cm² to about 16 kg/cm².

Many endoscopic surgical instruments utilize handle or levers to actuate the end effector assembly typically disposed at a distal end of the instrument. For example, actuation of the handle correspondingly actuates the jaw members. Once closed about tissue electrical energy is delivered to treat tissue. With open forceps, two opposing handles are pivotable relative to tone another to grasp tissue prior to energizing the jaw members.

In some instances, it may be beneficial for the surgeon to identify the resonance frequency of the tissue being sealed, cut or otherwise treated prior to electrosurgical activation. This frequency can be utilized to determine the appropriate electrosurgical energy output to enhance sealing, cutting or tissue treatment. In addition, detecting the resonance frequency of the tissue may help to identify nerves disposed in the tissue bundle prior to activation.

SUMMARY

As used herein, the term "distal" refers to the portion of the instrument or component thereof that is being described that is further from a user, while the term "proximal" refers to the portion of the instrument or component thereof that is being described that is closer to a user. Further, to the extent consistent, any of the aspects described herein may be used in conjunction with any of the other aspects described herein. As used herein the term "tissue" is meant to include variously-sized vessels.

Provided in accordance with aspects of the present disclosure is a surgical instrument including a housing having an elongated shaft extending distally therefrom and configured to support an end effector assembly at a distal end thereof. The end effector assembly includes first and second jaw members each having a tissue sealing plate disposed thereon and adapted to connect to an electrosurgical energy source for delivery thereto upon activation thereof. A sensor is disposed on one (or both) of the tissue sealing plates and is configured to communicate data relating to tissue disposed between the first and second jaw members to the electrosurgical energy source for correlation to a resonance frequency of the tissue. The resonance frequency of the tissue, in turn, is used to adjust one or more parameters associated with the delivery of electrosurgical energy to the tissue upon activation thereof.

In aspects according to the present disclosure, the one or more parameters associated with the delivery of electrosurgical energy to tissue includes: power, current, voltage, duration, and/or pulse width.

In aspects according to the present disclosure, the sensor includes an acoustic wave sensor, ultrasonic sensor or audio emitter. In other aspects according to the present disclosure, the resonance frequency of the tissue is used to identify tissue type.

In aspects according to the present disclosure, the resonance frequency of the tissue is used to identify one or more critical structures disposed within the tissue between the first and second jaw members. In other aspects according to the present disclosure, electrosurgical energy delivery to the tissue sealing plates is deactivated upon identification of one or more critical structures disposed within the tissue between the first and second jaw members. In still other aspects according to the present disclosure, a safety alarm is triggered upon identification of one or more critical structures disposed within the tissue between the first and second jaw members.

Provided in accordance with other aspects of the present disclosure is a system for treating tissue which includes a surgical forceps having a housing including an elongated shaft extending distally therefrom and configured to support an end effector assembly at a distal end thereof, the end effector assembly including first and second jaw members, each jaw member including a tissue sealing plate disposed thereon. A generator is configured to supply electrosurgical energy to one or both of the tissue sealing plates upon activation thereof. A sensor is disposed on one or both of the tissue sealing plates of the first and second jaw members, the sensor configured to communicate data relating to tissue disposed between the first and second jaw members to the electrosurgical energy source for correlation to a resonance frequency of the tissue. The resonance frequency of the tissue, in turn, is used to adjust one or more parameters associated with the delivery of electrosurgical energy to the tissue upon activation thereof.

In aspects according to the present disclosure, the one or more parameters associated with the delivery of electrosurgical energy to tissue includes: power, current, voltage, duration, and/or pulse width.

In aspects according to the present disclosure, the sensor includes is an acoustic wave sensor, ultrasonic sensor or audio emitter. In other aspects according to the present disclosure, the resonance frequency of the tissue is used to identify tissue type.

In aspects according to the present disclosure, the resonance frequency of the tissue is used to identify one or more critical structures disposed within the tissue between the first and second jaw members. In other aspects according to the present disclosure, electrosurgical energy delivery to the tissue sealing plates is deactivated upon identification of one or more critical structures disposed within the tissue between the first and second jaw members. In still other aspects according to the present disclosure, a safety alarm is triggered upon identification of one or more critical structures disposed within the tissue between the first and second jaw members.

Provided in accordance with other aspects of the present disclosure is a surgical instrument which includes a housing having an elongated shaft extending distally from the housing and configured to support an end effector assembly at a distal end thereof. The end effector assembly includes first and second jaw members each having a tissue sealing plate disposed thereon adapted to connect to an electrosurgical energy source for delivery thereto upon activation thereof. A sensor is disposed on one or both of the tissue sealing plates of the first and second jaw members and is configured to determine the resonance frequency of the tissue disposed between the first and second jaw members and communicate the resonance frequency of the tissue to the electrosurgical energy source. The electrosurgical energy source, in turn, is configured to adjust one or more parameters associated with the delivery of electrosurgical energy based on the resonance frequency of the tissue.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION

Figure 1A:
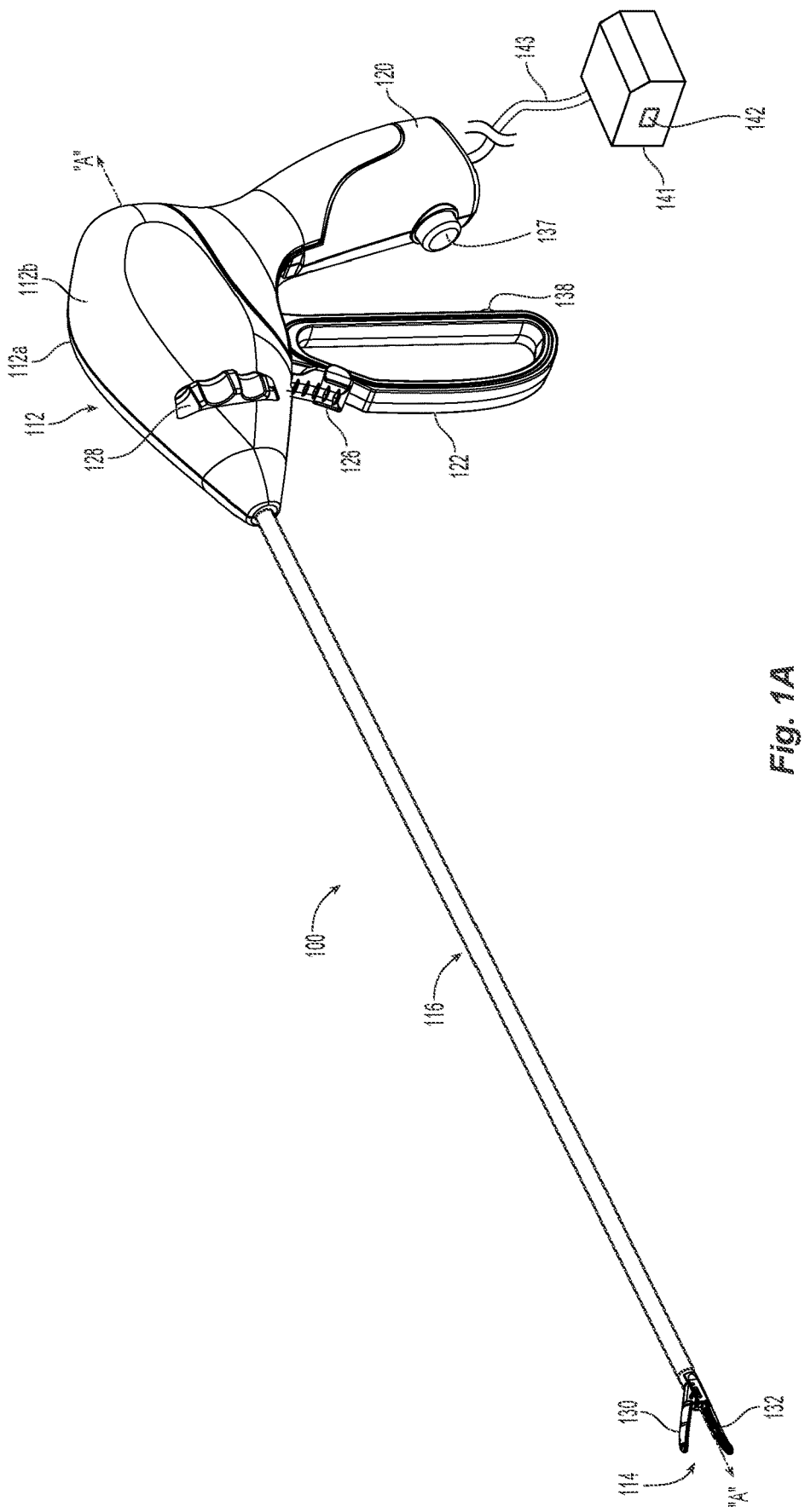
FIGS. 1A-1D are views of an endoscopic electrosurgical forceps including a housing, an elongated shaft, an end effector and one embodiment of a force gauge extending along the end effector.

Referring initially to FIG. 1A, an endoscopic electrosurgical forceps 100 generally includes a housing 112 that supports various actuators thereon for remotely controlling an end effector 114 through an elongated shaft 116. Although this configuration is typically associated with instruments for use in laparoscopic or endoscopic surgical procedures, various aspects of the present disclosure may be practiced with traditional open instruments and in connection with endoluminal procedures as well (See FIG. 2A). The housing 112 is constructed of a left housing half 112a and a right housing half 112b. The left and right designation of the housing halves 112a, 112b refer to the respective directions as perceived by an operator using the forceps 100. The housing halves 112a, 112b may be constructed of sturdy plastic, and may be joined to one another by adhesives, ultrasonic welding or other suitable assembly methods.

To mechanically control the end effector 114, the housing 112 supports a stationary handle 120, a movable handle 122, a trigger 126 and a rotation knob 128. The movable handle 122 is operable to move the end effector 114 between an open configuration wherein a pair of opposed jaw members 130, 132 are disposed in spaced relation relative to one another, and a closed or clamping configuration wherein the jaw members 130, 132 are closer together. Approximation of the movable handle 122 with the stationary handle 120 serves to move the end effector 114 to the closed configuration and separation of the movable handle 122 from the stationary handle 120 serves to move the end effector 114 to the open configuration. The trigger 126 is operable to extend and retract a knife blade 156 (FIG. 1B) through the end effector 114 when the end effector 114 is in the closed configuration. The rotation knob 128 serves to rotate the elongated shaft 116 and the end effector 114 about a longitudinal axis A-A extending through the forceps 100.

To electrically control the end effector 114, the stationary handle 120 supports a depressible button 137 thereon, which is operable by the user to initiate and terminate the delivery of electrosurgical energy to the end effector 114. The depressible button 137 is mechanically coupled to a switch (not shown) disposed within the stationary handle 120 which is in electrical communication with an electrosurgical generator 141 via suitable electrical wiring (not explicitly referenced) extending from the housing 112 through a cable 143 extending between the housing 112 and the electrosurgical generator 141. The generator 141 may include devices such as the LigaSure® Vessel Sealing Generator and the ForceTriad® Generator sold by Medtronic. The cable 143 may include a connector (not shown) thereon such that the forceps 100 may be selectively coupled electrically to the generator 141.

As mentioned above, the end effector 114 may be moved from the open configuration (FIG. 1B) wherein tissue (not shown) is received between the jaw members 130, 132, and the closed configuration (FIG. 1C), wherein the tissue is clamped and treated. The jaw members 130, 132 pivot about a pivot pin 144 (FIG. 1B) to move the end effector 114 to the closed configuration (FIG. 1C) of wherein sealing plates 148, 150 associated with respective jaw members 132, 130 provide a pressure to tissue grasped therebetween. In some embodiments, to provide an effective tissue seal, a pressure within a range between about 3 kg/cm$^2$ to about 16 kg/cm$^2$ and, desirably, within a working range of about 7 kg/cm$^2$ to about 13 kg/cm$^2$, may be applied to the tissue. Also, in the closed configuration, a separation or gap distance is maintained between the sealing plates 148, 150 by an array of stop members 154 (FIG. 1B) disposed on or adjacent the sealing plates 148, 150. The stop members 154 contact opposing surfaces on the opposing jaw member 130, 132 and prohibit further approximation of the sealing plates 148, 150. In some embodiments, to provide an effective tissue seal, an appropriate gap distance of about 0.001 inches to about 0.010 inches and, desirably, between about 0.002 inches to about 0.005 inches, may be provided. In some embodiments, the stop members 154 are constructed of a heat-resistant ceramic deposited onto the jaw members 130, 132. In other embodiments, the stop members 154 are constructed of an electrically non-conductive plastic molded onto the jaw members 130, 132, e.g., by a process such as overmolding or injection molding.

The upper and lower jaw members 130, 132 are electrically coupled to cable 143, and thus to the generator 141 (e.g., via respective suitable electrical wiring extending through the elongated shaft 116) to provide an electrical pathway to a pair of electrically conductive, tissue-engaging sealing plates 148, 150 disposed on the lower and upper jaw members 132, 130, respectively. The sealing plate 148 of the lower jaw member 132 opposes the sealing plate 150 of the upper jaw member 130. In some embodiments, the sealing plates 148 and 150 are electrically coupled to opposite terminals, e.g., positive or active (+) and negative or return (−) terminals associated with the generator 141. Thus, bipolar energy may be provided through the sealing plates 148 and 150 to tissue.

Alternatively, the sealing plates 148 and 150 may be configured to deliver monopolar energy to tissue. In a monopolar configuration, one or both sealing plates 148 and 150 deliver electrosurgical energy from an active terminal, e.g., (+), while a return pad (not shown) is placed generally on a patient and provides a return path to the opposite terminal, e.g., (−), of the generator 141. Each jaw member 130, 132 includes a jaw insert (not shown) and an insulator (not shown) that serves to electrically insulate the sealing plates 150, 148 from the jaw insert of the jaw members 130, 132, respectively.

Figure 1B:
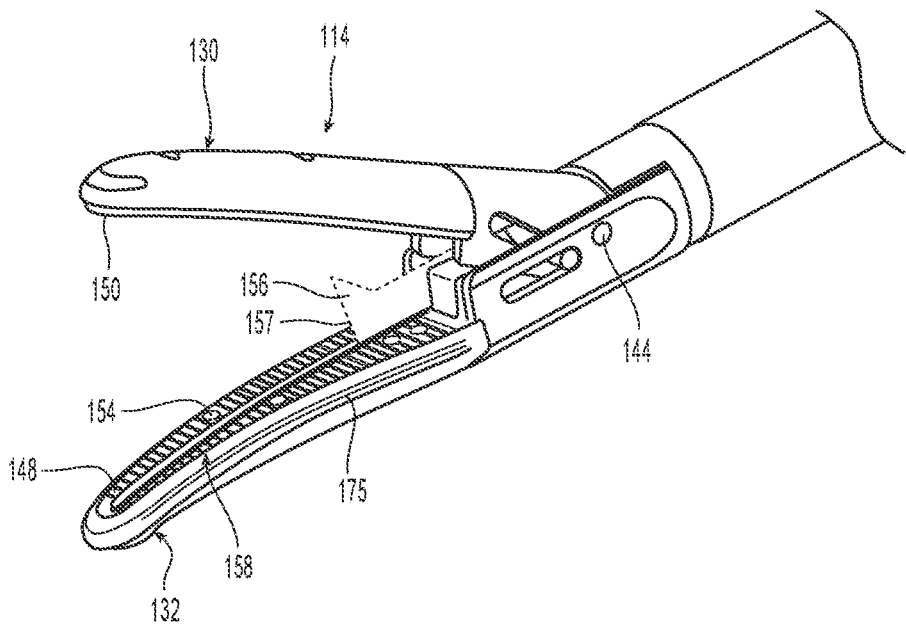
Figure 1C:
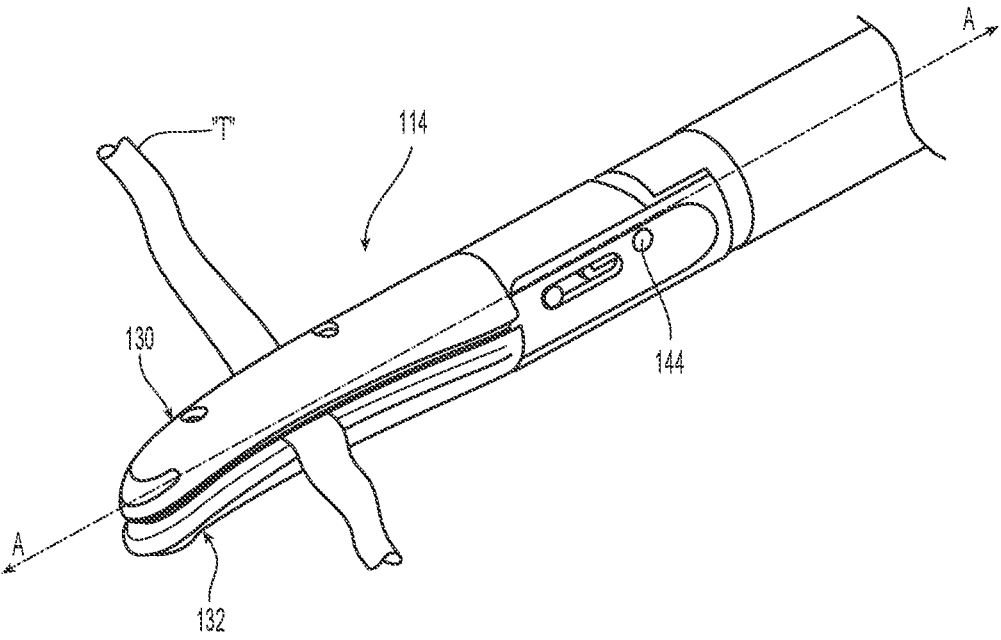
Figure 1D:
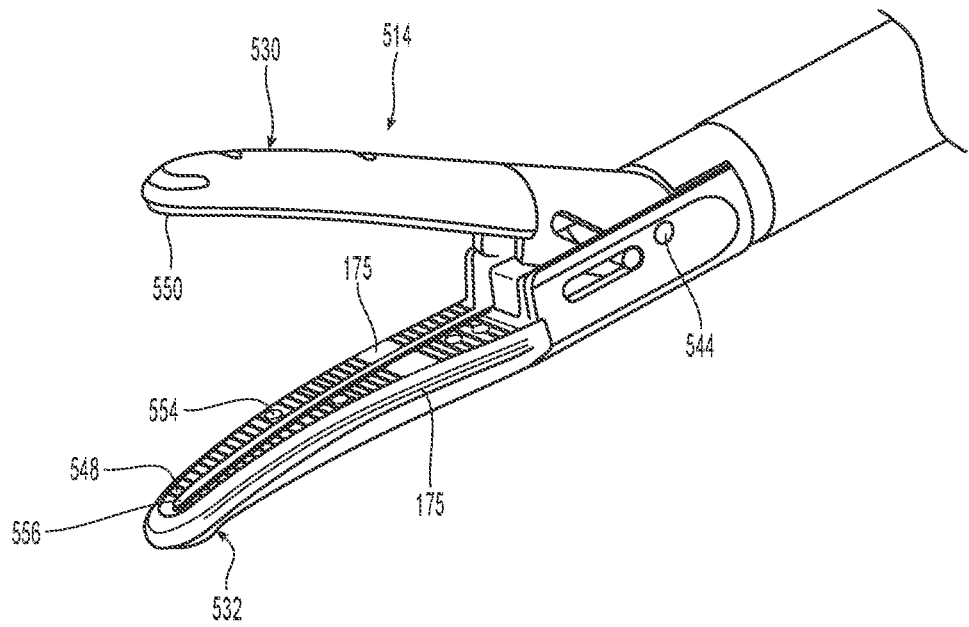

Electrosurgical energy may be delivered to the tissue through the electrically conductive seal plates 148, 150 to effect a tissue seal. Once a tissue seal is established, the knife blade 156 having a sharpened distal edge 157 may be advanced through a knife channel 158 defined in one or both jaw members 130, 132 to transect the sealed tissue. Although the knife blade 156 is depicted in FIG. 1B as extending from the elongated shaft 116 when the end effector 114 is in an open configuration, in some embodiments, extension of the knife blade 156 into the knife channel 158 when the end effector 114 is in the open configuration may be prevented by one or more lockout features. An electrosurgical knife 556 (FIG. 1D) may also be utilized to cut tissue. For example, U.S. Provisional Patent Application Ser. No. 63/056,113 filed Jul. 24, 2020 describes one such electrosurgical cutter and is incorporated by reference in its entirety herein.

Figure 2A:
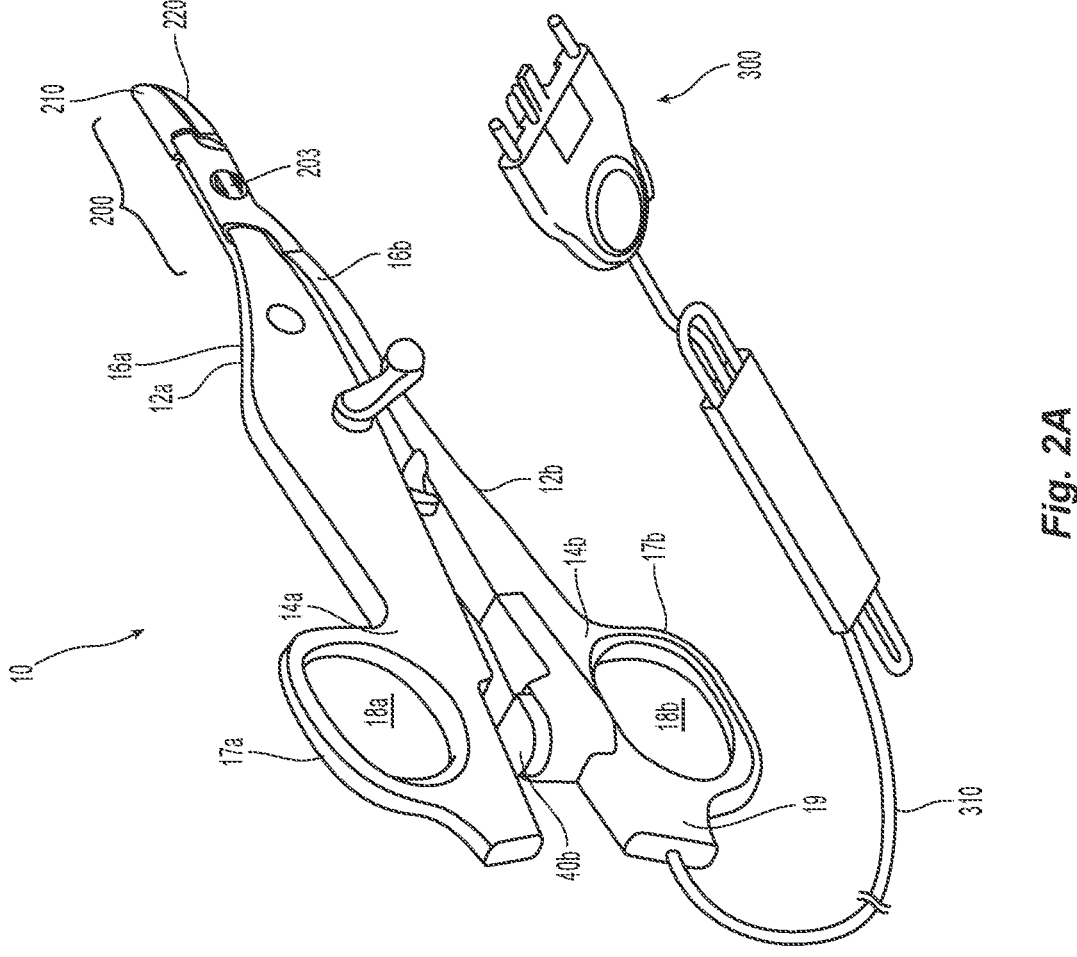
FIGS. 2A-2C are views of an open electrosurgical forceps including opposing shafts and an end effector assembly at a distal end thereof.
Figures 2B, 2C:
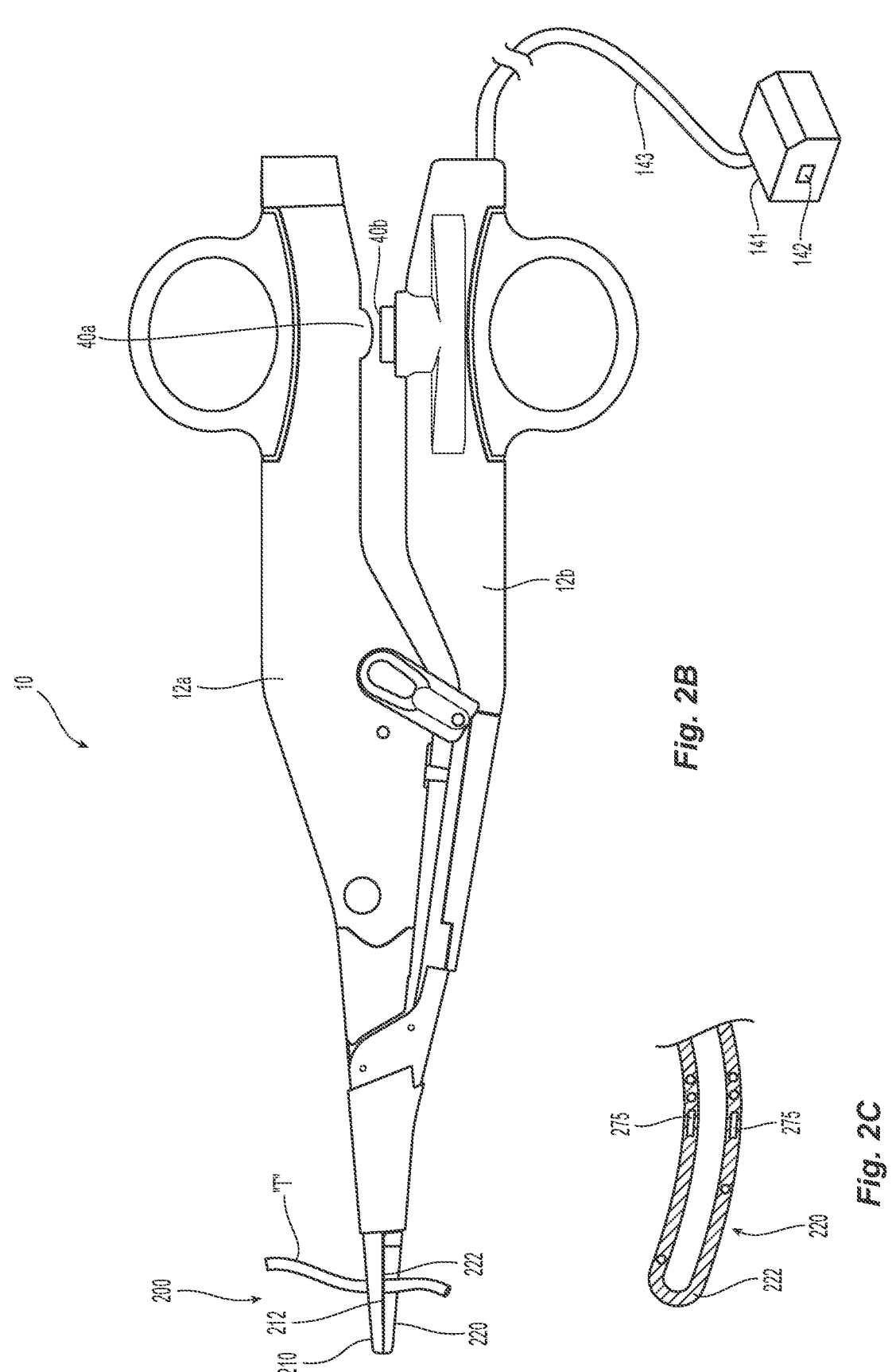

Referring now to FIGS. 2A-2C, an open forceps 10 contemplated for use in connection with traditional open surgical procedures is shown. For the purposes herein, either an open instrument, e.g., forceps 10, or an endoscopic instrument (FIGS. 1A-1D) may be utilized in accordance with the present disclosure. Obviously, different electrical and mechanical connections and considerations apply to each particular type of instrument; however, the novel aspects with respect to the end effector assembly and its operating characteristics remain generally consistent with respect to both the open and endoscopic configurations.

With continued reference to FIGS. 2A-2C, forceps 10 includes two elongated shafts 12a and 12b, each having a proximal end 14a and 14b, and a distal end 16a and 16b, respectively. Forceps 10 further includes an end effector assembly 200 attached to distal ends 16a and 16b of shafts 12a and 12b, respectively. End effector assembly 200 includes a pair of opposing jaw members 210, 220 that are pivotably connected about a pivot 203. Each shaft 12a and 12b includes a handle 17a and 17b disposed at the proximal end 14a and 14b thereof. Each handle 17a and 17b defines a finger hole 18a and 18b therethrough for receiving a finger of the user. Finger holes 18a and 18b facilitate movement of the shaft members 12a and 12b relative to one another between a spaced-apart position and an approximated position, which, in turn, pivot jaw members 210, 220 from an open position, wherein the jaw members 210, 220 are disposed in spaced-apart relation relative to one another, to a closed position, wherein the jaw members 210, 220 cooperate to grasp tissue therebetween.

Continuing with reference to FIGS. 2A-2C, one of the shafts, e.g., shaft 12b, includes a proximal shaft connector 19 that is designed to connect the forceps 10 to a source of electrosurgical energy such as an electrosurgical generator 141 (FIGS. 1A, 3B). Proximal shaft connector 19 secures an electrosurgical cable 310 to forceps 10 such that the user may selectively apply electrosurgical energy to electrically-conductive plates 212, 222 (See FIG. 2B) of jaw members 210, 220, respectively.

More specifically, cable 310 includes a plurality of wires (not shown) extending therethrough that has sufficient length to extend through one of the shaft members, e.g., shaft member 12b, in order to provide electrical energy to the conductive plates 212, 222 of jaw members 210, 220, respectively, of end effector assembly 200, e.g., upon activation of activation switch 40b (See FIGS. 2A and 2B). Other types activation switches are also contemplated, e.g., finger switch, toggle switch, foot switch, etc. and may be configured for this purpose. Cable 310 operably connects to generator 141 via plug 300.

Activation switch 40b is disposed at proximal end 14b of shaft member 12b and extends therefrom towards shaft member 12a. A corresponding surface 40a (FIG. 2B) is defined along shaft member 12a toward proximal end 14a thereof and is configured to actuate activation switch 40b. More specifically, upon approximation of shaft members 12a, 12b, e.g., when jaw members 210, 220 are moved to the closed position, activation switch 40b is moved into contact with, or in close proximity of surface 40a. Upon further approximation of shaft members 12a, 12b, e.g., upon application of a pre-determined closure force to jaw members 210, 220, activation switch 40b is advanced further into surface 40a to depress activation switch 40b. Activation switch 40b controls the supply of electrosurgical energy to jaw members 210, 220 such that, upon depression of activation switch 40b, electrosurgical energy is supplied to conductive surface 212 and/or conductive surface 222 of jaw members 210, 220, respectively, to seal tissue grasped therebetween. The electrical energy may be energy supplied through a proprietary Ligasure® sealing algorithm owned by Medtronic. The switch 40b may be disposed on either shaft 12a, 12b.

Referring back to FIG. 1C, once a vessel or tissue "T" or tissue is clamped between jaw members 130, 132 of end effector 114, the surgeon is ready to seal and cut the vessel or tissue "T" upon activation of the energy activation switch, e.g., switch 137, of endoscopic forceps 100. The switch 40b of open forceps 10 may be used for similar purposes, however, for the purposes herein, forceps 100 will be described hereinbelow.

A sensor 175 is disposed on one or both sealing plates 148, 150 of a respective jaw members 132, 130 and is configured to measure, or otherwise determine via communication with the generator 141, the resonant frequency of the tissue "T" (or vessel) disposed therebetween. A similar sensor 275 is disposed on one or both sealing plates, e.g., sealing plate 222, of jaw member 220 (FIG. 2C). For the purposes herein, sensors 175 and 275 are similar and, a such, only sensor 175 is further discussed below.

Sensor 175, 275 is configured to determine the tissue mass or tissue density and communicate this tissue data back to the generator 141 to correlate the resonant frequency based on a formula or look-up table. The resonant frequency is then utilized to determine the amount of electrosurgical energy sent to the jaw members 130, 132 for sealing the tissue "T", cutting the tissue "T" disposed between the jaw members or otherwise treating the tissue "T". Not only do the various tissue treatments typically require different energy parameters, e.g., power, voltage, duration, pulsing, pulse width, based on an energy curve, look-up table or algorithm, but knowing the resonant frequency may further enhance the tissue treatment for each activation.

As a result, the forceps 10, 100 performance and efficiency may be increased with each individual activation for the same or different tissue treatment during the course of an operation, e.g., sealing tissue then cutting tissue "T" with a specific tissue resonance in a first instance, then sealing and cutting different tissue "T" with a different tissue resonance in a subsequent instance.

Determining the tissue resonance prior to electrosurgical energy activation may also play an important role with surgical safety. For example, grasping the target tissue "T" between jaw members 130, 132 and then determining the resonance frequency may detect critical tissue structures, e.g., nerves and nerve bundles, prior to electrosurgical energy activation. An alarm 142 (e.g., regrasp alarm) may be triggered if a nerve is detected requiring the surgeon to reposition the jaw members 130, 132 about the tissue "T". In other instances, the generator 141 may be deactivated until the safety condition is satisfied, e.g., tissue "T" is repositioned and regrasped.

Sensor 175, 275 may be any type of sensor that can be used to communicate tissue data back to the generator 141 for correlation to the resonance frequency of the tissue "T". For example, sensor 175, 275 may be an acoustic wave sensor which utilizes microelectromechanical components that rely on the modulation of surface acoustic waves to sense a physical phenomenon. An acoustic wave sensor transduces an electrical signal into a mechanical wave which, unlike an electrical signal, can be easily influenced by physical phenomena. The mechanical wave is measured and the resonance frequency is determined by the sensor 175, 275 or communicated to the generator 141 for correlation to tissue resonance by an equation, look-up table or the like. Once the tissue resonance is determined, electrosurgical energy is delivered to the tissue "T" upon activation in accordance therewith and as per the particular tissue treatment parameters associated with sealing, cutting or otherwise treating tissue "T".

In another example, an ultrasonic sensor may be utilized which measures the distance and time through tissue "T" by emitting ultrasonic sound waves, and converts the reflected sound into an electrical signal which is conveyed to the generator 141 for correlation to tissue resonance by an equation, look-up table or the like. Different tissue types and masses will generate different reflection signals. Once the tissue resonance is determined, electrosurgical energy is delivered to the tissue "T" upon activation in accordance therewith and as per the particular tissue treatment parameters associated with sealing, cutting or otherwise treating tissue "T".

In other embodiments, an audio emitter may be utilized to collect tissue data for correlation by the generator 141.

As discussed herein the sensors and emitters are configure to generally interact with one another. More particularly, the emitter is configured to continuously emit and sweep through a range of frequencies, pre-determined to be of interest for detecting particular tissue types. The sensor would then detect tissue resonance at one or more frequencies within the range of frequencies that the emitter is sweeping. The resonance is detectable by measuring the amplitude (or power) of a particular frequency received by the sensor above a threshold.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as examples of particular embodiments. Those skilled in the art will envision other modifications within the scope and spirit of the claims appended hereto.

Although the foregoing disclosure has been described in some detail by way of illustration and example, for purposes of clarity or understanding, it will be obvious that certain changes and modifications may be practiced within the scope of the appended claims.

What is claimed is:

1. A surgical instrument, comprising:
a housing;
an elongated shaft extending distally from the housing;
an end effector assembly coupled to a distal end of the elongated shaft and including a first jaw member and a second jaw member with a respective first tissue sealing plate and a second tissue sealing plate, with each of the first and second tissue sealing plates configured for connection to an electrosurgical energy source for delivering electrosurgical energy to tissue; and
a sensor disposed on the first tissue sealing plate or the second tissue sealing plate and configured to communicate data relating to grasped tissue between the first jaw member and the second jaw member for:
determining a resonance frequency of the grasped tissue;
identifying, based on the determined resonance frequency, an additional structure disposed within the grasped tissue; and
based on the identified additional structure, adjusting one or more parameters associated with delivery of the electrosurgical energy to the tissue.

2. The surgical instrument according to claim 1, wherein the one or more parameters associated with the delivery of the electrosurgical energy to tissue includes at least one of power, current, voltage, duration, or pulse width.

3. The surgical instrument according to claim 1, wherein the sensor includes at least one of an acoustic wave sensor, ultrasonic sensor or audio emitter.

4. The surgical instrument according to claim 1, wherein the resonance frequency of the tissue is used to identify tissue type.

5. The surgical instrument according to claim 1, wherein the identified additional structure disposed within the grasped tissue comprises one or more critical structures unsuitable to receive the electrosurgical energy from the electrosurgical energy source.

6. The surgical instrument according to claim 5, wherein electrosurgical energy delivery to the tissue sealing plates is deactivated upon identification of the one or more critical structures disposed within the grasped tissue.

7. The surgical instrument according to claim 6, wherein a safety alarm is triggered upon identification of the one or more critical structures disposed within the grasped tissue.

8. A system for treating tissue, comprising:

a surgical forceps including a housing having an elongated shaft extending distally therefrom and an end effector assembly coupled to a distal end thereof, the end effector assembly including a first jaw member and a second jaw member with a respective first tissue sealing plate and a second tissue sealing plate;

a generator configured to supply electrosurgical energy to the first and second tissue sealing plates; and a sensor disposed on the first tissue sealing plate or the second tissue sealing plate and configured to communicate data relating to grasped tissue between the first jaw member and the second jaw member for:

determining a resonance frequency of the grasped tissue; and based on the determined resonance frequency, adjusting one or more parameters associated with delivery of electrosurgical energy to the tissue.

9. The system according to claim 8, wherein the one or more parameters associated with the delivery of the electrosurgical energy to tissue includes at least one of power, current, voltage, duration, or pulse width.

10. The system according to claim 8, wherein the sensor includes at least one of an acoustic wave sensor, ultrasonic sensor or audio emitter.

11. The system according to claim 8, wherein the resonance frequency of the tissue is used to identify tissue type.

12. The system according to claim 8, wherein the resonance frequency of the tissue is used to identify one or more critical structures disposed within the grasped tissue.

13. The system according to claim 12, wherein electrosurgical energy delivery to the tissue sealing plates is deactivated upon identification of the one or more critical structures disposed within the grasped tissue.

14. The system according to claim 13, wherein a safety alarm is triggered upon identification of the one or more critical structures disposed within the grasped tissue.

15. A system for treating tissue, comprising:

an electrosurgical instrument comprising an end effector coupled to an elongated shaft, the end effector comprising a first jaw member and a second jaw member with a respective first tissue sealing plate and a second tissue sealing plate;

one or more sensors disposed on the first tissue sealing plate or the second tissue sealing plate, the one or more sensors configured to communicate data relating to grasped tissue between the first jaw member and the second jaw member; and a generator coupled to the electrosurgical instrument and communicatively coupled to the one or more sensors, the generator configured to:

determine, based on the data from the one or more sensors, a resonance frequency of the grasped tissue;

identify, based on the determined resonance frequency, a critical structure present within the grasped tissue; and based on the identified critical structure, at least one of:

provide an indication for a clinician to reposition the end effector, or deactivate a supply of power to the electrosurgical instrument.

* * * * *